US008487054B2

(12) United States Patent
Murray et al.

(10) Patent No.: US 8,487,054 B2
(45) Date of Patent: Jul. 16, 2013

(54) BENZOPINACOL METALLOESTER POLYMERIZATION INITIATOR

(75) Inventors: Thomas James Murray, Chesterfield, MO (US); David L. Vines, Imperial, MO (US)

(73) Assignee: ELANTAS PDG, Inc., St. Louis, MO (US)

( * ) Notice: Subject to any disclaimer, the term of this patent is extended or adjusted under 35 U.S.C. 154(b) by 0 days.

(21) Appl. No.: 13/529,175

(22) Filed: Jun. 21, 2012

(65) Prior Publication Data

US 2012/0329967 A1    Dec. 27, 2012

Related U.S. Application Data

(60) Provisional application No. 61/499,933, filed on Jun. 22, 2011.

(51) Int. Cl.
*C08F 112/08* (2006.01)
*C07F 5/06* (2006.01)
*C07F 5/04* (2006.01)

(52) U.S. Cl.
USPC ........... 526/195; 526/226; 558/291; 558/289; 558/290; 556/175

(58) Field of Classification Search
USPC .... 526/195, 226; 558/289, 291, 290; 556/175
See application file for complete search history.

(56) References Cited

U.S. PATENT DOCUMENTS 3,256,310 A * 6/1966 Weil .............................. 558/289
4,117,017 A   9/1978 Morgan et al.
4,135,047 A   1/1979 Morgan

FOREIGN PATENT DOCUMENTS

EP    0 411 937 A2    2/1991

OTHER PUBLICATIONS

Ziemkowska, Wanda, et al.; "Reactions of Alkylalane Diolates with Water Synthesis, Characterisation and E-Caprolactone Polymerisation Activity of Novel Alane Benzopinacolates"; Journal of Organometallic Chemistry, pp. 2930-2939; vol. 689; Jul. 24, 2004.*
International Search Report, Form PCT/ISA/210, mailed Dec. 27, 2012, for corresponding PCT International Patent Application No. PCT/US2012/043459.
Written Opinion, Form PCT/ISA/237, mailed Dec. 27, 2012, for corresponding PCT International Patent Application No. PCT/US2012/043459.
Ziemkowska, Wanda, et al.; "Reactions of Alkylalane Diolates with Water Synthesis, Characterisation and ε-Caprolactone Polymerisation Activity of Novel Alane Benzopinacolates"; Journal of Organometallic Chemistry, pp. 2930-2939; vol. 689; Jul. 24, 2004.

* cited by examiner

*Primary Examiner* — William Cheung
(74) *Attorney, Agent, or Firm* — Curatolo Sidoti Co., LPA; Joseph G. Curatolo; Salvatore A. Sidoti

(57) ABSTRACT

A polymerization initiator based on boroesters of benzopinacol for curing unsaturated polymers is disclosed. Methods of preparing the benzopinacol boroester initiator and using the initiator in polymerization reactions are additionally disclosed.

21 Claims, No Drawings

BENZOPINACOL METALLOESTER POLYMERIZATION INITIATOR

CROSS REFERENCE TO RELATED APPLICATIONS

This application claims the benefit of the filing date under 35 U.S.C. 119(e) from U.S. Provisional Application For Patent Ser. No. 61/499,933 filed on Jun. 22, 2011, which is hereby incorporated by reference in its entirety.

TECHNICAL FIELD

The present disclosure relates to polymerization initiators for unsaturated polymers. The present disclosure more particularly relates to initiators that are based on metalloesters of benzopinacol that can be used in curing unsaturated polymers and/or unsaturated monomers.

BACKGROUND

Much of the work on low VOC unsaturated polyester systems has focused on the use of waxes as a means of reducing emission. During polymer resin cure, waxes, which are initially dissolved or dispersed in the resin, form a thin film on the surface of the fabricated article. The film acts as a physical barrier preventing styrene (or monomer) from evaporating from the surface of the curing part. This reduces styrene emissions. Unfortunately, this waxy film substantially diminishes interlaminar adhesion, reducing the strength of molded articles made using a multilaminate construction.

An alternative to the use of wax, is to reduce the molecular weight of the unsaturated polyesters. The lower molecular weight polyester requires the use of less styrene (monomer) to maintain an appropriate working viscosity. This approach suffers from side reactions and reduced physical properties. It is desirable to maintain the physical properties of the system while using conventional resin systems containing monomers such as styrene, vinyl toluene, acrylates or diallylphthalate.

Benzopinacol has been known for some time as a suitable radical polymerization initiator. However, the reactivity and end product properties have not been enough to overcome the extra preparation expense compared to peroxide based radical initiators. To improve reactivity and solubility, the potassium/sodium salts of benzopinacol have been reacted with di-, tri-, and tetra chlorosilanes or polyorganosilane/siloxane materials. These products have had limited commercial success however they have never been shown to reduce VOC emissions.

Silyl ethers of benzopinacol for use as free-radical initiators are known. No evaluation of VOC emissions or catalyzed shelf-life were examined.

A polyurethane derivatized benzopinacol initiator is known and was reported to behave as a "living" catalyst. The shelf-life or VOC emission reduction of the resulting polymers was not reported. Monofunctional isocyanates, such as phenylisocyanate, have also been used to derivatize benzopinacol. These initiators were also found to be "living" catalysts.

Bromoacetyl derivatives of benzopinacol are known as flame retardant initiators for the polymerization of unsaturated polyester (UPE) systems. Additionally, phosphorus and silyl ethers of benzopinacol as flame retardant initiators for UPE systems have been reported.

The synthesis of spirocyclic esters of boric acid, including benzopinacol has been demonstrated. However, the use of these complexes in initiating the polymerization of unsaturated polyester (UPE) resins containing monomers and/or the reduced VOC emissions of resulting UPE resins and catalyzed shelf-life has not been examined.

The synthesis of chiral borate complexes including the use of benzopinacol as a ligand has been demonstrated. However, the use of these complexes in initiating the polymerization of unsaturated polyester (UPE) resins containing reactive monomers and/or the reduced VOC emissions of resulting UPE resins and catalyzed shelf-life has not been elucidated.

SUMMARY

Provided is a polymerization initiator comprising a metalloester of benzopinacol or metalloester of a substituted benzopinacol. According to certain illustrative embodiments, the metalloester of benzopinacol comprises the following general formula and its structural isomers:

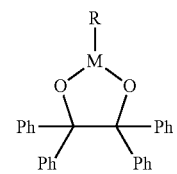

wherein M comprises a metal; and
wherein R comprises an organic moiety.

According to certain illustrative embodiments, the metalloester of benzopinacol may comprise a boroester of benzopinacol of the following formula and its structural isomers:

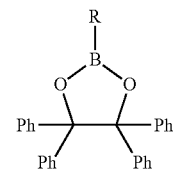

wherein R comprises an organic moiety in the formula.

According to certain illustrative embodiments, a boroester of benzopinacol comprises the following formula and its structural isomers:

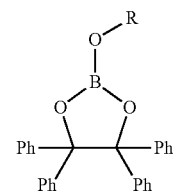

wherein R comprises an organic moiety.

Additionally provided is a process for preparing a polymerization initiator comprising metalloester of benzopinacol, the process comprising reacting benzopinacol or a derivative of benzopinacol with a metal that has volatile ligands, an alcohol and, optionally, an inert solvent. According to certain illustrative embodiments, the process for preparing the metalloester of benzopinacol comprises the following general reaction scheme:

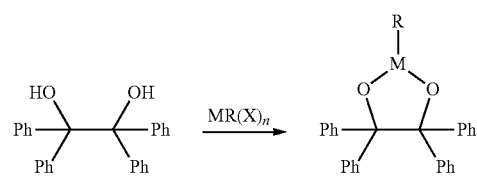

wherein M comprises a metal;
wherein R comprises organic moiety; and
wherein X comprises a leaving group.

According to certain illustrative embodiments, the process for preparing the metalloester of benzopinacol comprises the following general reaction scheme:

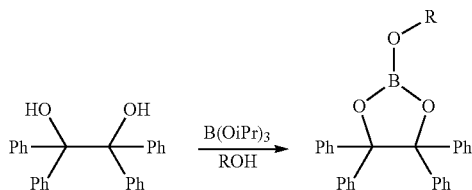

wherein R comprises organic moiety.

Further provided is a polymerization process comprising adding a polymerization initiator comprising a boroester of benzopinacol or a boroester of a benzopinacol derivative to reactive monomer and polymerizing said reactive monomer. According to certain illustrative embodiments, the metalloester of benzopinacol comprises the following general formula and its structural isomers:

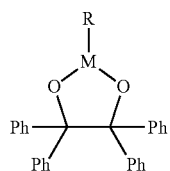

wherein M comprises a metal; and
wherein R comprises an organic moiety.

DETAILED DESCRIPTION

Disclosed is a polymerization initiator which exhibits reduced emissions of volatile organic compounds (VOC) compared to unsaturated polyester resin systems containing traditional initiators such as peroxides. Also disclosed is a process for preparing unsaturated polyester (UPE) resins containing reactive monomers, such as, without limitation, styrene (typically 30-40% by weight based on the total combined weight of the resin and the styrene), vinyl toluene (VT), or various acrylates. The use of the present polymerization initiator improves the catalyzed shelf life and cured physical and electrical properties of the UPE materials compared to the poor shelf-life for resin prepared using peroxide initiators such as t-butylbenzoylperoxide (TBP).

In order to achieve low VOC emissions, the process utilizes a metalloester of benzopinacol or benzopinacol derivative, such as a boroester of benzopinacol or a benzopinacol derivative, as the initiator for UPE resins containing styrene or other volatile monomers. The metalloesters of benzopinacol or metalloesters of benzopinacol derivatives are represented by the various chemicals formulas set forth in this disclosure and their respective structural isomers. Thus, the polymerization initiators may comprise a blend of a certain chemical formula and one or more of its structural isomers. The radical polymerization initiators used in the process reduce VOC emissions when the resins are cured into articles of commerce using open-curing (molding) techniques.

The boroesters of benzopinacol may be prepared by reacting benzopinacol with trialkylborate and another high boiling functional alcohol as reported by Huskens. The trialkylborate maybe dissolved in an inert solvent. According to certain illustrative embodiments, the trialkylborate may comprise tri(isopropyl)borate, tri(n-butyl)borate, tri(t-butyl)borate, boratrane, boron allyloxide, tri(ethoxy)borate, tri(propyl)borate, tri(methoxyethoxy)borate, and tri(methyl)borate. The tri(isopropyl)borate (1 mol) may be dissolved in an inert solvent, such as toluene. There is no limitation on the type of solvent or combinations of solvents that may be used in the process for preparing the boroester of benzopinacol and other solvents may be used as long as they are nonreactive. Benzopinacol (1 mol) and another mono, di-, or tri-functional alcohol (ROH, 0-1 mol) is added to the dissolved trialkylborate. The mixture is subjected to vacuum distillation (rotary evaporator) to remove the solvent under reduced pressure. The process is continued until all the solvent and isopropyl alcohol were removed.

According to certain illustrative embodiments, one or more of the phenyl rings on the benzopinacol molecule may be substituted. For example, and without limitation, one or more of the phenyl rings on the benzopinacol molecule may include alkyl, aryl, alkoxy, or halogen substitutions which provide derivatives of benzopinacol that function as free radical initiators for polymerization of unsaturated polyester resins with reactive monomers such as styrene or acrylates. The organic moiety R for all disclosed embodiments of the metalloester of benzopinacol maybe selected from alkyl, alkoxy, aryl and thioether groups.

The above described illustrative process for preparing metalloester of benzopinacol is shown in Scheme 1 below:

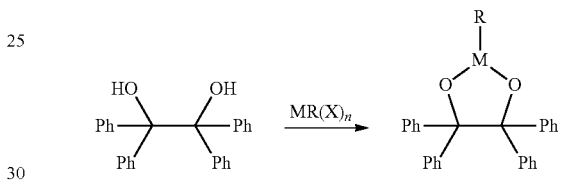

wherein M comprises a metal;
wherein R comprises an organic moiety;
wherein X comprises a leaving group; and
wherein n comprises 1 to 3.

According to certain illustrative embodiments, benzopinacol boroester polymerization initiators may be represented by the following general formulas and respective structural isomers:

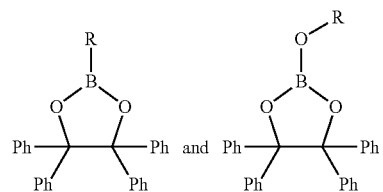

wherein R comprises an organic moiety in both of the above general formulas.

An illustrative process for preparing boroester of benzopinacol is shown in Scheme 2 below:

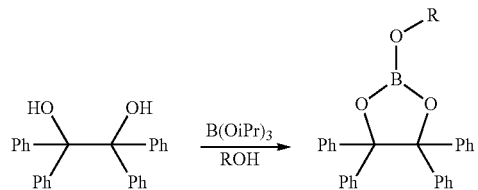

The processes for preparing various illustrative embodiments of the benzopinacol boroester polymerization initiators are shown in the following reaction schemes:

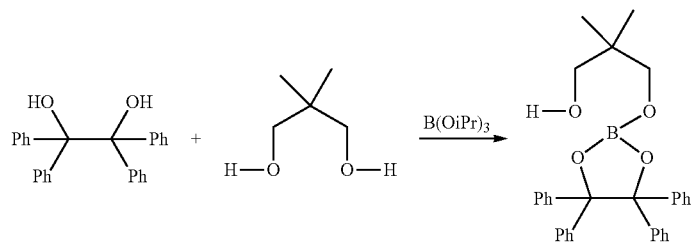
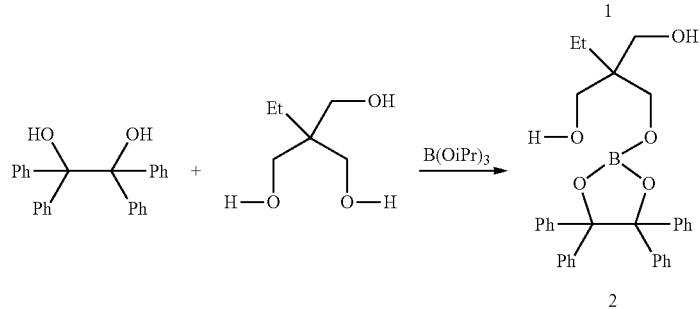
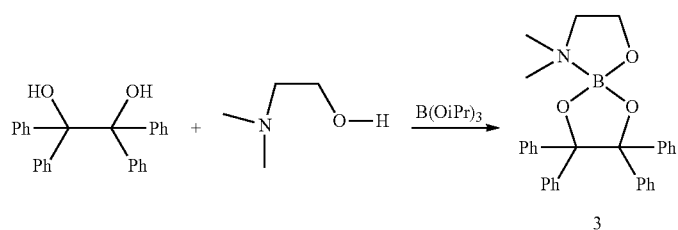
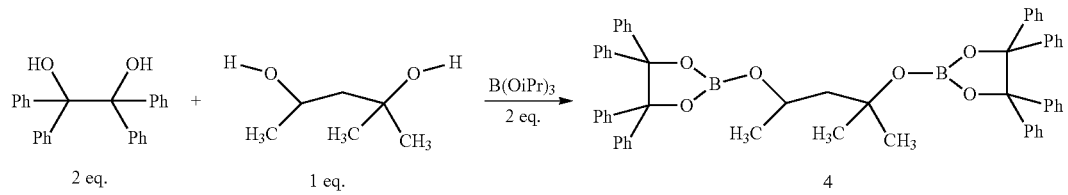
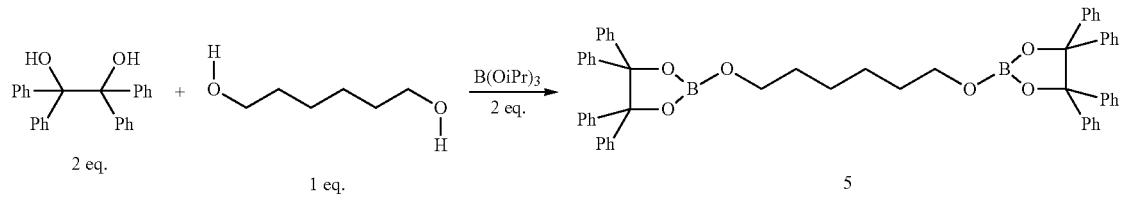
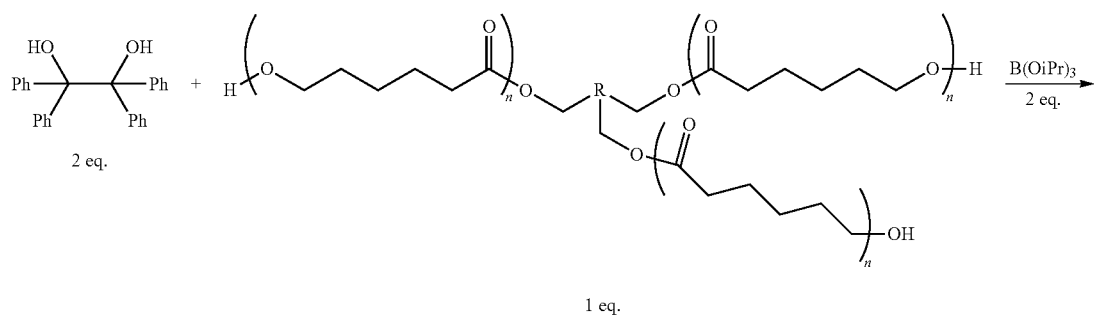

-continued
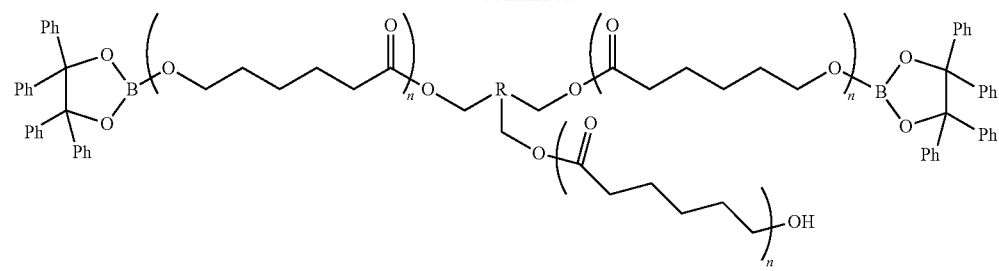
6
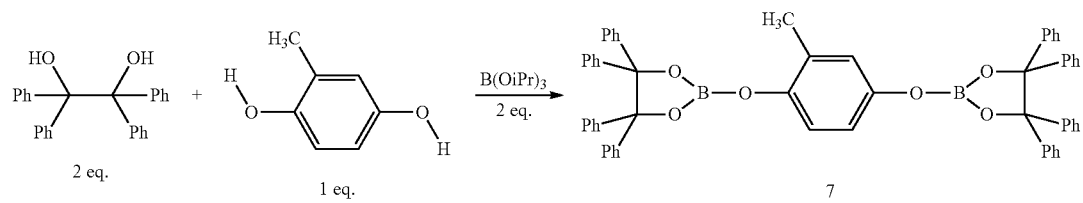
7
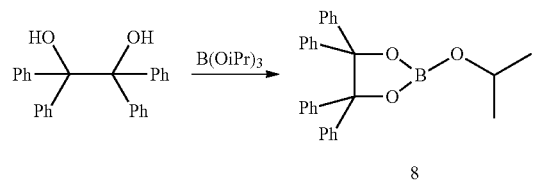
8
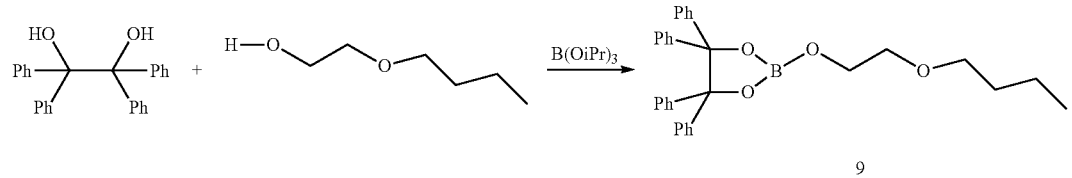
9
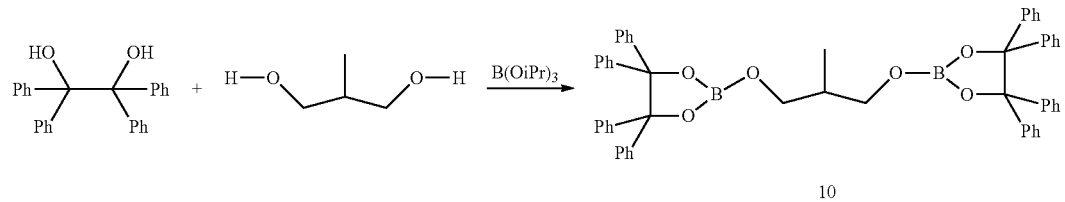
10
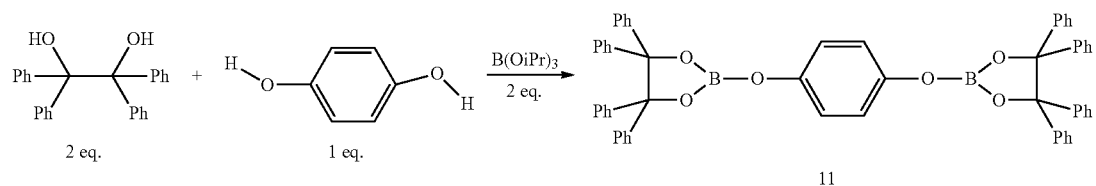
11
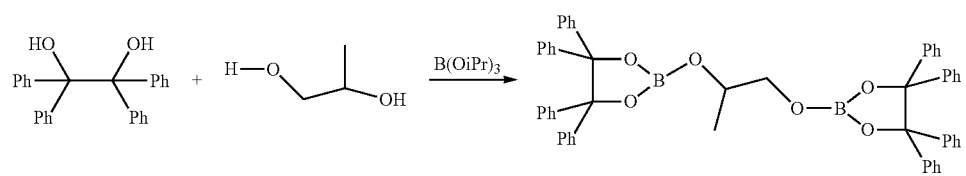
12

According to certain illustrative embodiments, aluminum ester of benzpinacol polymerization initiators may be represented by the following general formulas and their respective structural isomers:

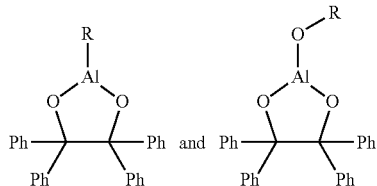

wherein R comprises an organic moiety in both of the above general formulas.

A process for preparing an illustrative embodiment of the benzopinacol metalloester polymerization initiator is shown in the following reaction scheme:

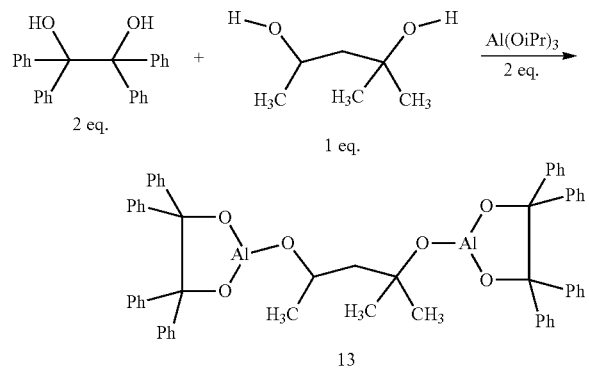

According to a further illustrative embodiment, the boroester of benzopinacol may be prepared from the reaction of boric acid in combination with benzopinacol and another mono, di-, or tri-functional alcohol. This illustrative process may be performed in an inert solvent or combination of inert solvents with the removal of the solvent and water.

It is well known how unsaturated polyester resins can be synthesized. The progress of the reaction can be followed by measuring the acid value of the mixture. Glycols are added along with unsaturated diacids that include maleic anhydride and the mixture is heated to 355-430° F. with some form of agitation such as stirring. Dicyclopentadiene can also be added with cracking (Diels-Alder chemistry) or under hydrolysis conditions to add to the polymer. Volatiles are removed, preferably by distillation and the acid value (ASTM D1639-90) and viscosity (ASTM D1545-89) of the mixture are monitored until the desired end-point is reached. In addition the reaction with the glycols can be carried out in the presence of oils containing ethylenic unsaturation such as soybean oil. The reaction mixture is cooled and monomer is added to give the desired UPE resins. Inhibitors can be added to the monomer for extending storage stability of the resin.

Examples of unsaturated carboxylic acids and corresponding anhydrides useful in the present process include maleic acid, fumaric acid, itaconic acid and maleic anhydride. In addition other acids, anhydrides or esters of the acids can be added to modify the chemical composition. Non-limiting examples of such acids and anhydrides include phthalic acid, isophthalic acid, terephthalic acid, tetrahydrophthalic anhydride, phthalic anhydride, nadic anhydride, methylnadic anhydride, hexahydrophthalic anhydride, dimethyl terephthalate and the like. Maleic acid and maleic anhydride are used in illustrative embodiments.

A wide variety of polyols can be used in the process of the preparation of the benzopinacol boroester initiator. Suitable polyols include common diols such as ethylene glycol, propylene glycol, 1,3-propanediol, 1,4-propanediol, 1,4-butanediol, 2,2-dimethyl-1,3-propanediol, 2-methyl-1,3-propanediol, glycol ethers such as diethylene glycol and dipropylene glycol, and polyoxyalkylene glycols like polyoxyethylene glycol and polyoxypropylene glycol. Triols and higher functional polyols such as glycerol, trimethylol propane and oxyalkylated adducts thereof can also be used. Preferably, the polyols are aliphatic or alicyclic and optionally contain C—O—C linkages.

Examples of oils containing unsaturation include castor oil, peanut oil, linseed oil, safflower oil, olive oil, cotton oil, rapeseed oil, soybean oil, and tung oil, and mixtures thereof. In addition, fatty acids could be used in combination with or instead of the oil. An example would be ricinoleac acid instead of castor oil. Modified oils such as epoxidized soybean oil may also be used.

Other materials commonly used in the synthesis of unsaturated polyester resins, such as solvents, isomerization and/or condensation catalyst, promoters, etc. can be used in the process of the invention. Examples of solvents are those commonly known in the art and include but are not limited to hexane, cyclohexane, benzene, toluene, xylene, and mixtures of solvents. Commonly used inhibitors include hydroquinone, p-benzoquinone, di-t-butylhydroquinone, t-butylcatechol, phenothiazine, and the like. Catalysts used to promote the condensation reaction include p-toluene sulfonic acid, methane sulfonic acid, zinc salts (e.g. acetate), organotin compounds (dibutyl tin oxide) and other materials known to those skilled in the art. Isomerization catalysts include organic amines such as morpholine and piperidine.

Commercially available UPE resins used in this invention include Pedigree® 600 Styrene, Pedigree® 600 VT and Pedigree® 70 VT. All were uncatalyzed but can be cured with conventional peroxide initiators such as TBP or dicumylperoxide. The present disclosure is not limited to UPE resins used in electrical insulating materials but could also be used in molding materials and any other resin systems using UPE resins with reactive monomers such as styrene.

In general, the process may be carried out by mixing the initiator into the resin either by means of high shear dispersing blade or dissolution with time and temperature. Some derivatives are more soluble than others and require less energy to disperse the material into the UPE resin while others require more force to achieve a stable dispersion. The initiator can also be pre-dissolved/dispersed in another liquid prior to adding to the UPE resin solution. The initiator can be added to the UPE resin material at levels of about 0.1 to about 10%. According to alternative embodiments, the resin loading level is about 1 to about 2% to UPE resin material.

The following examples are set forth to describe methods of synthesizing various illustrative embodiments of the benzopinacol boroester initiator in further detail and to illustrate exemplary methods of preparation and use of the initiator. The following examples following should not be construed as limiting the initiator, the methods of preparing the initiator or method of using the initiator in polymerization reactions in any manner.

Boroester Initiator Synthesis

Synthesis of Boroester Initiator 1: Triisopropyl borate, 0.106 moles (20 grams), benzopinacol, 0.106 moles (38.8 grams), and neopentyl glycol, 0.106 moles (11.02 grams) were dissolved in 1000 grams of ethyl acetate and mixed for about two hours at room temperature. Ethyl acetate and evolved isopropanol were removed by rotovap at 50° C. until the mixture was reduced to a paste. 1000 grams of toluene was added and the rotovap procedure was repeated. Another 1000 grams of toluene was added and the rotovap procedure was again repeated. The result of the synthesis reaction was a white waxy solid. This white waxy solid was spread out in a tray and dried at about 40° C. The resulting material was crushed to a fine white powder.

Synthesis of Boroester Initiator 2: Boroester Initiator 2 was prepared by the same synthesis reaction as set forth above for the synthesis of Boroester Initiator 1 except that neopentyl glycol was replaced with 0.106 moles (14.2 grams) of trimethylol propane. The reactants were dissolved in 1000 grams of toluene and 755 grams of ethyl acetate. The result was a fine white powder.

Synthesis of Boroester Initiator 3: Boroester Initiator 3 was prepared by the same synthesis reaction as set forth above for the synthesis of Boroester Initiator 1 except that neopentyl glycol was replaced with 0.106 moles (9.43 grams) of dimethylethanolamine. The reactants were dissolved in 1000 grams of toluene. The result was a fine white powder.

Synthesis of Boroester Initiator 4: Boroester Initiator 4 was prepared by the same synthesis reaction as set forth above for the synthesis of Boroester Initiator 1 except that neopentyl glycol was replaced by 0.053 moles (6.25 grams) of hexylene glycol. The reactants were dissolved in toluene. The result was a fine white powder Synthesis of Boroester Initiator 5: Boroester Initiator 5 was prepared by the same synthesis reaction as set forth above for the synthesis of Boroester Initiator 1 except that neopentyl glycol was replaced with 0.053 moles (6.25 grams) of 1,6-hexanediol. The reactants were dissolved in 500 g of toluene and 500 grams of ethyl acetate. The result was a thick white paste.

Synthesis of Boroester Initiator 6: Boroester Initiator 6 was prepared by the same synthesis reaction as set forth above for the synthesis of Boroester Initiator 1 except that neopentyl glycol was replaced with 0.053 moles (28.6 grams) of CAPA 3050, a caprolactone triol commercially available from Perstorp UK Limited, (Warrington, Cheshire, UK). Reactants were dissolved in 500 grams of toluene and 500 grams of ethyl acetate. After rotovap the result was a white rubbery material. It was dissolved in ethyl acetate and toluene and rotovapped, and then repeated with toluene and then ethyl acetate and dried at 40° C. The result was a white viscous almost paste-like material.

Synthesis of Boroester Initiator 7: Triisopropyl borate, 0.0107 moles (2.01 grams), benzopinacol, 0.0107 moles (3.9 grams), and toluhydroquinone, 0.0054 moles (0.67 grams) were dissolved in ethyl acetate and toluene This reaction mixture was rotovapped at 50° C. until the mixture was reduced to a paste, mixed with about 35 grams of toluene and subjected to the rotovap procedure twice more, then dried at 40° C. The result was a thick white paste.

Synthesis of Boroester Initiator 8: Triisopropyl borate, 0.053 moles (9.97 grams) and benzopinacol, 0.053 moles (19.4 grams) were dissolved in toluene and ethyl acetate at room temperature and rotovapped at 50° C. The rotovapped mixture was then mixed with toluene and subjected to the rotovap procedure twice more, then dried at 40° C. Result was a thick white paste.

Synthesis of Boroester Initiator 9: Boroester Initiator 9 was prepared by the same synthesis method as Boroester Initiator 7, except that toluhydroquinone was replaced by 0.0107 moles (1.26 grams) of ethyleneglycol monobutyl ether. The result was a white solid which was ground to a fine white powder.

Synthesis of Boroester Initiator 10: Boroester Initiator 10 was prepared by the same synthesis method as Boroester Initiator 7 except that toluyhdroquinone was replaced by 0.0054 moles (0.59 grams) of 2-methyl-1,3-propanediol. The result was a white solid which was ground to a fine white powder.

Synthesis of Boroester Initiator 11: Boroester Initiator 11 was prepared by the same synthesis method as Boroester Initiator 7 except that toluhydroqionone was replaced by 0.0054 moles (0.59 grams) of hydroquinone. The result was a white solid which was ground to a fine white powder.

Synthesis of Boroester Initiator 12: 0.053 moles (19.4 grams) of benzopinacol, 0.053 moles (9.96 grams) of triisopropyl borate, and 0.0265 moles (2.01 grams) of propylene glycol were dissolved in 250 grams of toluene and 250 grams of ethyl acetate. Toluene, ethyl acetate and isopropyl alcohol were removed by rotovap at 50 C until the mixture was reduced to a paste. The rotovapped mixture was mixed with about 500 grams of toluene and subjected to the rotovap procedure again. The rotovapped mixture was again mixed with about 500 grams of toluene and subjected to the rotovap procedure again. The resulting paste was dried at 40 C to a white solid, which was ground to a fine white powder.

Synthesis of Metalloester Initiator 13: 0.053 moles (19.4 grams) of benzopinacol, 0.053 moles (10.81 grams) of aluminum isopropoxide, and 0.0265 moles (3.127 grams) of hexylene glycol were mixed with 762 grams of toluene and heated to about 48 C. The resulting mixture was rotovapped at 50 C to a paste. The paste was mixed with about 500 grams of toluene and subjected to the rotovap procedure again. The resulting paste was again mixed with about 500 grams of toluene and subjected to the rotovap procedure again. The resulting paste was dried at 40 C and crushed to a fine white powder.

Synthesis of Metalloester Initiator 14: 0.053 moles (19.4 grams) of benzopinacol, 0.053 moles (13.62 grams) of nickel acetylacetonate, and 0.0265 moles (3.127 grams) of hexylene glycol were mixed with 1570 grams of toluene, 466 grams of ethyl acetate, and 50 grams of xylene and heated to about 43 C. The mixture was rotovapped to a paste and mixed with about 400 grams of toluene and 100 grams of xylene and subjected to the rotovap procedure again. This was repeated one more time. The resulting green paste was dried at 40 C and crushed to a fine green powder.

POLYMERIZATION EXAMPLE 1

Boroester Initiator 1 (1 weight percent) was mixed into Pedigree® 600 Styrene with a cowles blade until a dispersion was obtained. The dispersion exhibited a viscosity of about 327 cps at 25° C. as measured by Brookfield viscometry. A sunshine gel time of 5.6 minutes was obtained at 125° C. and 21 minutes at 100° C. Thermal analysis showed a polymerization onset temperature of 128° C. by modulated DSC.

Magnet wire (MW35) was formed into tight helical coils, dipped into the resin solution and cured in an oven for about 2 hours at about 150° C. The bond strength of the resin to the magnet wire was measured on an Instron using the 3-point break method at 25° C. in accordance with ASTM D2519. Excellent bond strength of 34 lbs was observed.

A 20 g sample of the catalyzed resin was cured in an oven at about 150° C. for about one hour. The weight loss was 2.5% on curing (% weight loss=100−100×((weight of sample after cure−weight of dish)/weight of material added to dish before curing)). A measure of the cure is in the hardness of the sample as measured by the Barber-Colman method. A reading of 87 by this method confirmed good cure of the resin. Thermogravimetric analysis also confirmed good cure of the resin by recording a temperature of 333° C. for 10% weight loss. Accelerated aging of the resin at 50° C. lasted 38 days before gelling, thereby demonstrating good shelf-life.

POLYMERIZATION EXAMPLE 2

A polymerization reaction was carried out as set forth above for Example 1 except Boroester Initiator 2 was mixed in at 1% into Pedigree® 600 Styrene. The data is summarized in Table 1 below. Excellent reactivity, low weight loss on curing and extended shelf-life was observed with Boroester Initiator 2 compared with the control samples.

POLYMERIZATION EXAMPLE 3

A polymerization reaction was carried out as set forth above for Example 1 except Boroester Initiator 3 was mixed in at 1% into Pedigree® 600 Styrene. The data is summarized in the Table 1 below. Good reactivity, low weight loss on curing and extended shelf-life was observed with Boroester Initiator 3 compared to the control materials.

COMPARATIVE POLYMERIZATION EXAMPLE 1

A polymerization reaction was carried out as set forth above for Example 1 except t-butylbenzoylperoxide (TBP) was mixed in at 1% into Pedigree® 600 Styrene. The data is summarized in Table 1 below. Weight loss on curing (13%) was considerably higher than the boroester benzopinacol initiators. Without being bound to any particular theory, these results would imply that this system would emit far greater quantities of volatile organic compounds (VOC) compared to the systems based on the present benzopinacol boroester initiators. Accelerated aging (3 days) was also considerably worse than with the benzopinacol boroester initiator materials.

COMPARATIVE POLYMERIZATION EXAMPLE 2

A polymerization reaction was carried out as set forth above for Example 1 except benzopinacol silyl ether, as prepared in U.S. Pat. No. 4,145,507, was mixed in at 1% into Pedigree® 600 Styrene. The data is summarized in Table 1 below. Weight loss on curing (13%) was considerably higher than the benzopinacol boroester initiators. Without being bound to any particular theory, these results would imply that this system would emit far greater quantities of VOC compared to the boroester catalyzed materials. Accelerated aging (3-5 days) was also considerably worse than with benzopinacol boroester initiator materials.

These examples further show that that the use of the benzopinacol boroester initiator emits far less volatile organic compounds compared to traditional initiators using standard resin/monomer formulations. Equivalent physical properties were observed while increasing the catalyzed shelf-life as demonstrated by the accelerated aging results.

To further demonstrate the VOC reduction using the present benzopinacol boroester initiators, ASTM Method D-6053 was performed on the initiators used above in Comparative Polymerization Examples 1 and 2, and Polymerization Examples 1-3. The data is compiled in the chart below. Both the 2 gram and 10 gram methods were examined. A 20-60% reduction in VOC was observed using the boroester initiators compared to the control materials.

TABLE 2

| VOC ASTM D-6053 | Initiator | 2 gram | 10 gram |
| --- | --- | --- | --- |
| Comparative Example 1 | 1% TBP | 2.34 lbs/gal | 1.47 lbs/gal |
| Comparative Example 2 | 1% BP Silylether | 2.03 lbs/gal | 1.45 lbs/gal |
| Example 1 | 1% Boroester 1 | 1.80 lbs/gal | 0.63 lbs/gal |
| Example 2 | 1% Boroester 2 | 1.75 lbs/gal | 0.61 lbs/gal |
| Example 3 | 1% Boroester 3 | 1.90 lbs/gal | 0.63 lbs/gal |

POLYMERIZATION EXAMPLE 4

A polymerization reaction was carried out as set forth above for Example 1 except Boroester Initiator 3 was mixed in at 1% into Pedigree® 70 VT. The data is summarized in Table 3 below. Excellent reactivity, low weight loss on curing and extended shelf-life was observed with the Boroester Initiator 3 compared with Comparative Example 4. Comparative Examples 5 and 6 exhibited good shelf-life, however, each of them were considerably worse than the present benzopinacol boroesters with respect to VOC reduction.

POLYMERIZATION EXAMPLE 5

A polymerization reaction was carried out as set forth above for Example 1 except Boroester Initiator 2 was mixed in at 1% into Pedigree® 70 VT. The data is summarized in the Table 3 below. Excellent reactivity, low weight loss on curing and extended shelf-life was observed with Boroester Initiator

TABLE 1

| Boroester Initiator | 1 | 2 | 3 | TBP (Comparative 1) | BP Silylether (Comparative 2) |
| --- | --- | --- | --- | --- | --- |
| amount | 1% | 1% | 1% | 1% | 1% |
| viscosity | 327 | 345 | 360 | 300 | 310 |
| 125 C. sunshine gel | 5.6 | 6.1 | 12.6 | 6.2 | 3 |
| 100 C. sunhine gel | 21 | 20.4 | 73.4 | 23.8 | 4.3 |
| DSC onset ° C. | 128 | 129 | 145 | 121 | 111 |
| Peak Max ° C. | 140 | 141 | 155 | 130 | 124 |
| Joules/gram | 325 | 326 | 360 | 360 | 338 |
| Bond strength @25° C. Helical coils 2 hr 150 C. | 34 | 38 | 28 | 36 | 26 |
| Barber Colman hardness | 87 | 86 | 88 | 88 | 87 |
| wt loss, 20 g puck, 1 hr 150 C. | 2.5% | 4% | 3.1% | 13.1% | 12.5% |
| TGA 10% wt loss, ° C. | 333 | 321 | 325 | 322 | 329 |
| 50 C. stability, tube | 38 days | 29 days | 51 days | 3 days | 3-5 days |

These results set forth in Polymerization Examples 1-3 show that mono-, di-, and tri-functional alcohols in combination with benzopinacol and trialkylborate provided an effective polymerization initiator for unsaturated monomers.

2 compared with Comparative Example 4. Comparative Examples 5 and 6 gave good shelf-life, however each of them were considerably worse than the present benzpinacol boroesters initiators with respect to VOC reduction.

POLYMERIZATION EXAMPLE 6

A polymerization reaction was carried out as set forth above for Example 1 except Boroester Initiator 1 was mixed in at 1% into Pedigree® 70 VT. The data is summarized in Table 3 below. Excellent reactivity, low weight loss on curing and extended shelf-life was observed with Boroester Initiator 1 compared with Comparative Example 4. Comparative Examples 5 and 6 gave good shelf-life, however, each of them were considerably worse than the present benzopinacol boroesters with respect to VOC reduction.

COMPARATIVE POLYMERIZATION EXAMPLE 3

A polymerization reaction was carried out as set forth above for Example 1 except t-butylbenzoylperoxide (TBP) was mixed in at 1% into Pedigree® 70 VT. The data is summarized in Table 3 below. Weight loss on curing (11%) was considerably higher than the boroester benzopinacol initiators. Without being bound to any particular theory, this would imply that this system would emit far greater quantities of VOC compared to the boroester catalyzed materials. Accelerated aging (5 days) was also considerably worse than with the present benzopinacol boroester initiators.

COMPARATIVE POLYMERIZATION EXAMPLE 4

A polymerization reaction was carried out as set forth above for Example 1 except dicumylperoxide was mixed in at 1% into Pedigree® 70 VT. The data is summarized in Table 3 below. Weight loss on curing (15%) was considerably higher than the boroester benzopinacol initiators. Without being bound to any particular theory, this would imply that this system would emit far greater quantities of VOC compared to the boroester catalyzed materials.

COMPARATIVE POLYMERIZATION EXAMPLE 5

A polymerization reaction was carried out as set forth above for Example 1 except unmodified benzopinacol was mixed in at 1% into Pedigree® 70 VT. The data is summarized in Table 3 below. Weight loss on curing (14%) was considerably higher than the present boroester benzopinacol initiators. Without being bound to any particular theory, would imply that this system would emit far greater quantities of VOC compared to the boroester catalyzed materials.

These results set forth in Polymerization Examples 4-6 show that mono-, di-, and tri-functional alcohols in combination with benzopinacol and trialkylborate provide an effective initiator in another reactive monomer system, such as vinyl toluene (VT). These examples show that the present process provides initiators that emit far less volatile organic compounds compared to traditional initiators using standard resin/monomer formulations. Equivalent physical properties were observed while increasing the catalyzed shelf-life as demonstrated by the accelerated aging results.

POLYMERIZATION EXAMPLE 7

A polymerization reaction was carried out as set forth above for Example 1 except Boroester Initiator 4 was mixed in at 1% into Pedigree® 600 Styrene. The data is summarized in Table 4 below. Excellent reactivity, low weight loss on curing and extended shelf-life was observed with the present benzopinacol boroester initiator compared with the comparative examples.

POLYMERIZATION EXAMPLE 8

A polymerization reaction was carried out as set forth above for Example 1 except Boroester Initiator 5 was mixed in at 1% into Pedigree® 600 Styrene. The data is summarized in Table 4 below. Excellent reactivity, low weight loss on curing and extended shelf-life was observed with the present benzopinacol boroester initiator compared with the comparative examples.

POLYMERIZATION EXAMPLE 9

A polymerization reaction was carried out as set forth above for Example 1 except Boroester Initiator 6 was mixed in at 2% into Pedigree® 600 Styrene. The data is summarized in Table 4 below. Excellent reactivity, low weight loss on curing and extended shelf-life was observed with the present benzopinacol boroester initiator compared with the comparative examples.

COMARATIVE POLYMERIZATION EXAMPLE 6

A polymerization reaction was carried out as set forth above for Example 1 except unmodified benzopinacol was mixed in at 1% into Pedigree® 600 Styrene. The data is summarized in Table 4 below. Weight loss on curing (15%) was considerably higher than the boroester benzopinacol ini-

TABLE 3

| Initiator | Example 4 Boroester 3 | Example 5 Boroester 2 | Example 6 Boroester 1 | Comparative Example 3 TBP | Comparative Example 4 Dicup | Comparative Example 5 benzopinacol |
|---|---|---|---|---|---|---|
| amount | 1% | 1% | 1% | 1% | 1% | 1% |
| viscosity | 570 | 590 | 575 | 495 | 495 | 595 |
| 125 C. gel | 12.3 | 5.7 | 5 | 5.9 | 7.6 | 4.6 |
| 100 C. gel | 58.9 | 20.8 | 20.4 | 26 | 45 | 13.2 |
| Bond strength 25 C. | 11.58 | 24.4 | 22 | 26.86 | 22.92 | 25.64 |
| Bond strength 150 C. | 3.42 | 4.5 | 4.6 | 5 | 4.2 | 6.72 |
| 20 g puck 1 hr 150 C. wt loss % | 3.9 | 2.7 | 2.3 | 11 | 14.7 | 13.8 |
| hardness | 84 | 82 | 81 | 85 | 83 | 80 |
| 50 C. stability | 74 days | 18 days | 19 days | 5 days | 36 days | 33 days | tiators. Without being bound to any particular theory, this would imply that this system would emit far greater quantities of VOC compared to the boroester catalyzed materials.

TABLE 4

|  | Example 7 | Example 8 | Example 9 | Comparative Example 6 |
|---|---|---|---|---|
| catalyst | Boroester 4 | Boroester 5 | Boroester 6 | benzopinacol |
| amount | 1% | 1% | 2% | 1% |
| viscosity | 405 | 436 | 405 | 410 |
| 125 C. sunshine gel | 4.5 | 7.4 | 4.7 | 4.3 |
| 100 C. sunshine gel | 13.3 | 38.9 | 17.6 | 15 |
| DSC onset ° C. | 124 | 135 | 129 | 123.63 |
| Peak Max ° C. | 137 | 147 | 142 | 136.56 |
| Joules/gram | 359 | 372 | 377 | 357.4 |
| Bond strength @25° C. Helical coils 2 hr 150 C. | 26.2 | 30.6 | 33.6 | 27.9 |
| Bond strength @150° C. Helical coils 2 hr 150 C. | 10.9 | 8.28 | 11.1 | 11.3 |
| Barber Colman hardness | 90 | 92 | 88 | 91 |
| wt loss, 20 g puck, 2 hr 150 C. | 2.7% | 3.6% | 3.3% | 14.8% |
| TGA 10% wt loss | 343 | 341 | 338 | 337 |
| 50 C. stability, tube | 30 days | 35 days | 39 days | 30 days |

These results set forth in Polymerization Examples 7-9 show that bis-, and multi-functional boroesters are effective polymerization initiators for unsaturated monomers, such as styrene. These examples show that the present process provides initiators that emit far less volatile organic compounds compared to traditional initiators using standard resin/monomer formulations. Equivalent physical properties were observed while increasing the catalyzed shelf-life as demonstrated by the accelerated aging results.

POLYMERIZATION EXAMPLE 10

A polymerization reaction was carried out as set forth above for Example 1 except Boroester Initiator 7 was mixed in at 1% into Pedigree® 600 Styrene. The data is summarized in Table 5 below. Excellent reactivity, low weight loss on curing and extended shelf-life was observed with the present benzopinacol boroester initiator compared with the comparative examples.

POLYMERIZATION EXAMPLE 11

A polymerization reaction was carried out as set forth above for Example 1 except Boroester Initiator 8 was mixed in at 1% into Pedigree® 600 Styrene. The data is summarized in Table 5 below. Excellent reactivity, low weight loss on curing and extended shelf-life was observed with the present benzopinacol boroester initiator compared with the comparative examples.

TABLE 5

|  | Example 10 | Example 11 |
|---|---|---|
| catalyst | Boroester 7 | Boroester 8 |
| amount | 1% | 1% |
| viscosity | 355 | 340 |
| 125 C. sunshine gel | 7.3 | 6.3 |
| 100 C. sunshine gel | 48.4 | 28.4 |
| DSC onset ° C. | 177 | 131 |
| Peak Max ° C. | 184 | 143 |
| Joules/gram | 328 | 392 |
| Bond strength @25° C. Helical coils 2 hr 150 C. | 29.94 | 28.84 |
| Bond strength @150° C. Helical coils 2 hr 150 C. | 6.84 | 10.08 |
| Barber Colman hardness | 92 | 92 |
| wt loss, 20 g puck, 2 hr 150 C. | 6.40% | 5.60% |
| TGA 10% wt loss |  |  |
| 50 C stability, tube | >5 months | 44 days |

Effective aromatic and mono-functional benzopinacol boroester initiators are demonstrated by Polymerization Examples 10-11. These examples show that the present process provides initiators that emit far less volatile organic compounds compared to traditional initiators using standard resin/monomer formulations. Equivalent physical properties were observed while increasing the catalyzed shelf-life as demonstrated by the accelerated aging results.

POLYMERIZATION EXAMPLE 12

A polymerization reaction was carried out as set forth above for Example 1 except Boroester Initiator 13 was mixed in at 1% into Pedigree® 600 Styrene. The data is summarized in Table 6 below. Excellent reactivity, low weight loss on curing and extended shelf-life was observed with the present benzopinacol aluminum ester initiator compared with the comparative examples.

POLYMERIZATION EXAMPLE 13

A polymerization reaction was carried out as set forth above for Example 1 except Boroester Initiator 14 was mixed in at 1% into Pedigree® 600 Styrene. The data is summarized in Table 6 below. Excellent reactivity, low weight loss on curing and extended shelf-life was observed with the present benzopinacol nickel ester initiator compared with the comparative examples.

TABLE 6

|  | Boroester 13 | Boroester 14 |
|---|---|---|
| amount | 1% | 1% |
| viscosity | 385 | 380 |
| 125 C. sunshine gel | 5.8 | 5.2 |
| 100 C. sunshine gel | 21.6 | 19.9 |
| DSC onset ° C. | 127 | 127 |
| Peak Max ° C. | 139 | 139 |
| Joules/gram | 344 | 342 |
| Bond strength @25° C. Helical coils 2 hr 150 C. | 32.46 | 29.4 |
|  | 9.24 | 5 |
| Barber Colman hardness | 92 | 92 |
| wt loss, 20 g puck, 2 hr 150 C. | 3.30% | 4.80% |
| TGA 10% wt loss | 337° C. | 324° C. |
| 50 C. stability, tube | 36 days | >5 months |
| appearance | slight haze | clear, green |

While the polymerization initiators and methods of preparation and use have been described in connection with various illustrative embodiments, it is to be understood that other similar embodiments may be used or modifications and additions may be made to the described embodiments for performing the same function disclosed herein without deviating there from. The embodiments described above are not necessarily in the alternative, as various embodiments may be combined to provide the desired characteristics. Therefore, the initiators and methods should not be limited to any single embodiment, but rather construed in breadth and scope in accordance with the recitation of the appended claims.

The invention claimed is:

1. A polymerization initiator comprising a metalloester of benzopinacol or a metalloester of a derivative of benzopinacol of the following general formula:

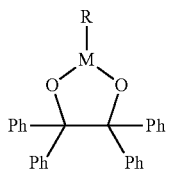

wherein M comprises a metal; and
wherein R comprises an organic moiety.

2. The polymerization initiator of claim 1, wherein said metalloester of benzopinacol comprises a boroester of benzopinacol of the following general formula:

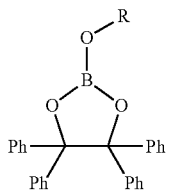

wherein R comprises an organic moiety.

3. The polymerization initiator of claim 2, wherein said boroester of benzopinacol comprises the following formula 1:

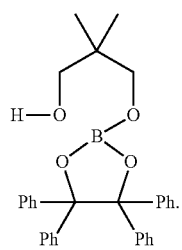

4. The polymerization initiator of claim 2, wherein said boroester of benzopinacol comprises the following formula 2:

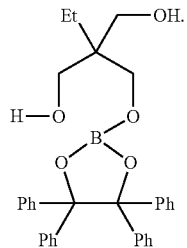

5. The polymerization initiator of claim 2, wherein said boroester of benzopinacol comprises the following formula 3:

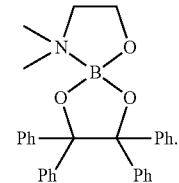

6. The polymerization initiator of claim 2, wherein said boroester of benzopinacol comprises the following formula 4:

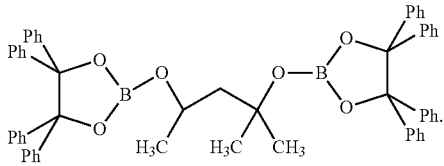

7. The polymerization initiator of claim 2, wherein said boroester of benzopinacol comprises the following formula 5:

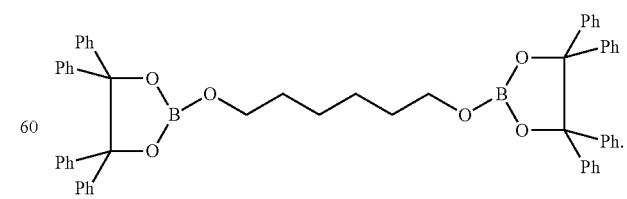

8. The polymerization initiator of claim 2, wherein said boroester of benzopinacol comprises the following formula 6:

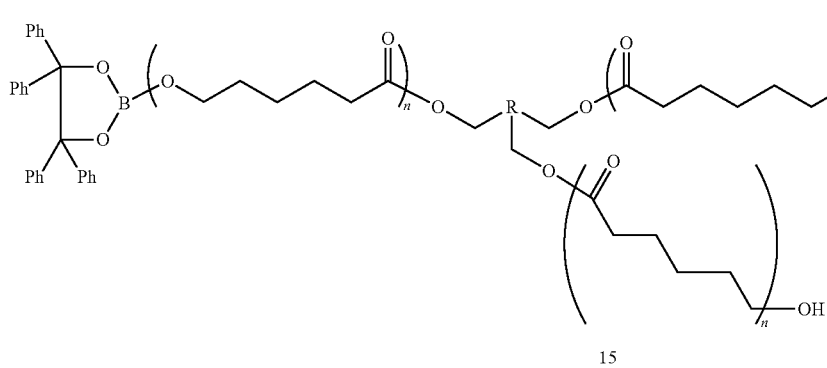

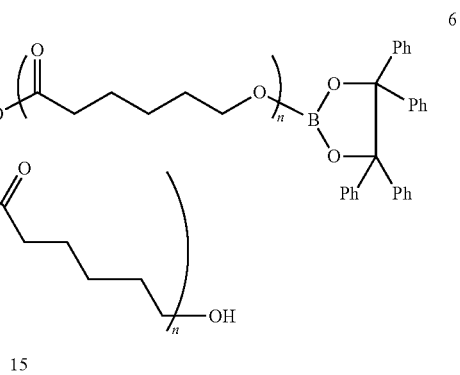

wherein n is an integer from 0 to 5.

9. The polymerization initiator of claim 2, wherein said boroester of benzopinacol comprises the following formula 7:

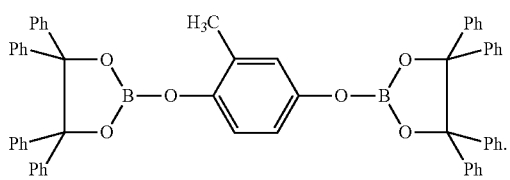

10. The polymerization initiator of claim 2, wherein said boroester of benzopinacol comprises the following formula 8:

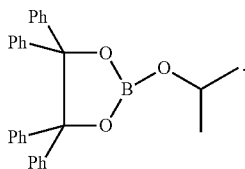

11. The polymerization initiator of claim 2, wherein said boroester of benzopinacol comprises the following formula 9:

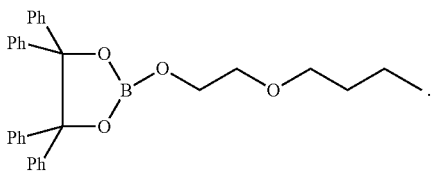

12. The polymerization initiator of claim 2, wherein said boroester of benzopinacol comprises the following formula 10:

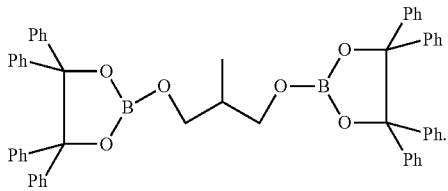

13. The polymerization initiator of claim 2, wherein said boroester of benzopinacol comprises the following formula 11:

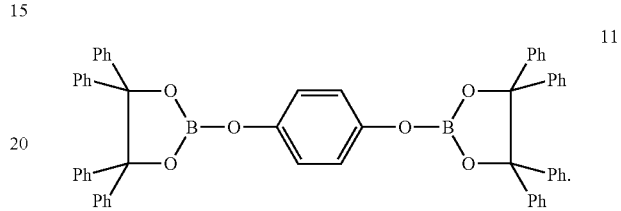

14. The polymerization initiator of claim 2, wherein said boroester of benzopinacol comprises the following formula 12:

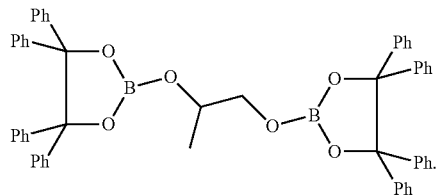

15. The polymerization initiator of claim 1, wherein said metalloester of benzopinacol comprises the following formula:

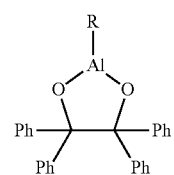

wherein R comprises an organic moiety.

16. The polymerization initiator of claim 15, wherein said metalloester of benzopinacol comprises the following formula:

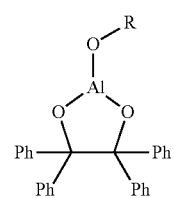

wherein R comprises an organic moiety.

17. The polymerization initiator of claim 16, wherein said metalloester of benzopinacol comprises the following formula 13:

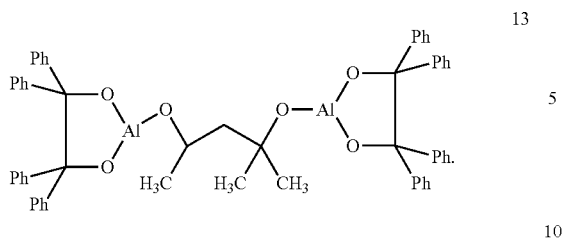

18. A process for preparing a metalloester of benzopinacol of claim 1 comprising reacting benzopinacol or a derivative of benzopinacol with a metal or metal-containing compound, an alcohol and, optionally, an inert solvent.

19. The process for preparing a metalloester of benzopinacol of claim 18, comprising reacting benzopinacol or a derivative of benzopinacol with a borate or boric acid, an alcohol and, optionally, an inert solvent.

20. The process for preparing a boroester of benzopinacol of claim 19, wherein said borate comprises a trialkylborate.

21. The process for preparing a boroester of benzopinacol of claim 19, wherein said alcohol comprises a functional polyol selected from the group consisting of a mono-functional alcohols, di-functional alcohol, and tri-functional alcohols.

* * * * *